(12) United States Patent
Ekdahl et al.

(10) Patent No.: US 6,689,116 B1
(45) Date of Patent: Feb. 10, 2004

(54) DIAPER THAT INCLUDES WELDABLE FASTENER DEVICES

(75) Inventors: Joakim Ekdahl, deceased, late of Tidaholm (SE), by Kurt Ekdahl, Kerstin Ekdahl, legal representatives; Elisabeth Lakso, Stenungsund (SE); Anders Silverstrand, Mölnlycke (SE); Anders Strålin, Torslanda (SE); Eva Simmons, Molndal (SE); Hannele Nurmi, Ronnang (SE); Anna-Karin Jonbrink, Lerum (SE)

(73) Assignee: SCA Hygiene Products AB, Gothenburg (SE)

(*) Notice: Subject to any disclaimer, the term of this patent is extended or adjusted under 35 U.S.C. 154(b) by 0 days.

(21) Appl. No.: 09/743,286

(22) PCT Filed: Jul. 1, 1999

(86) PCT No.: PCT/SE99/01199

§ 371 (c)(1),
(2), (4) Date: Nov. 20, 2001

(87) PCT Pub. No.: WO00/01339

PCT Pub. Date: Jan. 13, 2000

(30) Foreign Application Priority Data

Jul. 6, 1998 (SE) ............................................. 9802429

(51) Int. Cl.[7] ............................ A61F 13/15; A61F 13/20
(52) U.S. Cl. ...................... 604/391; 604/365; 604/367; 604/389; 604/364; 604/372
(58) Field of Search ................................. 604/364, 367, 604/374, 385.01, 385.03, 386–391, 365–366, 372

(56) References Cited

U.S. PATENT DOCUMENTS

| | | | | |
|---|---|---|---|---|
| 5,219,342 A | * | 6/1993 | Hatch et al. | 604/370 |
| 5,300,057 A | | 4/1994 | Miller et al. | |
| 5,901,419 A | * | 5/1999 | Widlund et al. | 24/304 |
| 6,123,695 A | * | 9/2000 | Skog et al. | 604/386 |
| 6,149,639 A | * | 11/2000 | Lundberg et al. | 604/386 |
| 6,290,687 B1 | * | 9/2001 | Skog et al. | 604/391 |

FOREIGN PATENT DOCUMENTS

| | | |
|---|---|---|
| DE | 38 35 927 | 4/1990 |
| EP | 0 809 951 | 12/1997 |
| WO | WO 95/29200 A1 * | 11/1995 |
| WO | WO 00/01335 A1 * | 1/2000 |

* cited by examiner

*Primary Examiner*—Karin Reichle
(74) *Attorney, Agent, or Firm*—Young & Thompson

(57) ABSTRACT

An absorbent article, such as a diaper, a pants-type diaper, an incontinence protector or a pants-like sanitary napkin, having a front part, a rear part and an intermediate central part. The article includes an absorbent body enclosed between an inner, liquid-permeable sheet and a liquid-impermeable outer sheet, and fastener devices for releasably connecting side-portions of the front and rear parts. The fastener devices are made of a renewable material. The fastener devices are welded to at least one of the sheets of the article and the fastener devices and the sheets are made of a material having a glass transition temperature which lies between 50–60° C. and a melting point which lies between 140–180° C., preferably between 150–175° C.

12 Claims, 5 Drawing Sheets

DIAPER THAT INCLUDES WELDABLE FASTENER DEVICES

FIELD OF INVENTION

The present invention relates to an absorbent article, such as a diaper, a pants-type diaper, an incontinence protector or a pants-like sanitary napkin, said article including a front part, a rear part and an intermediate central part and also including an absorbent body which is enclosed between a liquid-permeable inner sheet or top sheet and a liquid-impermeable outer sheet or backing sheet, and fastener devices by means of which the side-portions of the front and rear parts can be releasably fastened together either directly or indirectly. The fastener devices are located on the same side of the longitudinal symmetry line of said article and are produced from a renewable material.

BACKGROUND OF THE INVENTION

The use of fastener devices that include mechanically coacting elements is becoming more and more popular. Manufacturers are beginning to give absorbent articles a pants-like configuration. Many requirements are placed on mechanically coacting elements of this nature. Among other things, they should be easy to open and close and soft enough to ensure that a baby or other person wearing said article will not be injured by the fastener elements. They must also be made of relatively inexpensive material because of the one-time use nature of the products to which they are attached. Such fastener devices are often made of plastic material, such as polypropylene for instance, and represent a not-insignificant percentage of the material consumed in article manufacture when seen as a whole. It is well known that the oil from which the raw material for plastic materials derives is not a renewable resource and the use of plastic materials draws on the earth's natural oil resources. It is known from EP-A2-0 809 952 to manufacture fastener devices from a water-soluble or biologically degradable resin, wherewith the fastener device has an underside which becomes adhesive upon contact with water. Polylactic acid is mentioned as one possible material from which these fastener devices can be made.

Since the use of gluing as a joining method has the drawbacks of incurring high material costs and production complications incurred by waste and delays in the process line, it is preferred to weld the fastener devices to the side-portions of the products. Plastic material is thermally welded or ultrasonically welded to the outer sheets and backing sheets normally used in the aforesaid products. However, a relatively large amount of energy is consumed in producing weld joins of sufficient strength between outer sheets and plastic fastener devices by heat welding or ultrasonic welding processes. The maximum welding speed, i.e. the highest speed, at which a web of material can be moved past a welding unit while producing weld joins of sufficient strength constitutes a limiting parameter with respect to the number of products of the aforesaid kind that can be produced per unit of time in a continuous article manufacturing line. There is thus a need to reduce the amount of energy consumed in fastening such fastener devices, so as to achieve the advantage of enabling higher welding speeds to be used in addition to saving energy.

The object of the present invention is to satisfy these needs and to enable the fastener devices to be made from renewable material.

SUMMARY OF THE INVENTION

These objects are achieved in accordance with the invention with an absorbent article, such as a diaper, a pants-like diaper, an incontinence protector or a pants-like sanitary napkin, of the aforesaid kind, wherein said article is characterised in that the fastener devices are welded to at least one of the outer sheets of said article; and in that the outer sheet or sheets to which said fastener devices is/are fastened is/are made of a material that has a glass transition temperature that lies between 50–60° C. and a melting point or melting point that lies between 140–180° C., preferably between 150–175° C.

In one preferred embodiment, the fastener devices and the outer sheet or sheets to which said devices is/are fastened is/are produced mainly or entirely from polylactic acid. The fastener devices each include two mutually coacting elements of which one element is fastened to the front side-portion of the article and the other element is fastened to the rear side-portion of said article and said coacting elements are fastened to either the same or to different outer sheets of said article. When the coacting elements are fastened to different outer sheets, both of said sheets are made of a material that has a glass transition temperature which lies between 50–60° C. and a melting temperature which lies between 140–180° C., preferably between 150–175° C.

The fastener devices may be made of polylactic acid, a lactic acid copolymer that includes caprolactone for instance, plasticized or softened polylactic acid or a laminate (coextrudate) that consists of a combination of these materials.

In a first variant, the fastener devices include two mechanically coacting fastener elements of which one element includes a part which projects out from the plane of said element and which can be inserted into a recess or aperture of corresponding form in the other element, the direction of insertion being parallel to the plane of said elements. The fastener elements are fastened to the liquid-impervious outer sheet.

In another variant, each of the fastener devices includes two mechanically coacting fastener elements which each include hooked parts that have a mutually complementary form. The fastener elements of this variant are fastened to different outer sheets.

In a third variant, each of the fastener devices includes two mechanically coacting fastener elements that include parts which can be snapped into each other.

In a fourth variant, the fastener devices each include two mechanically coacting fastener elements which include hook and loop members.

In a fifth variant, the fastener devices each include an adhesive tab.

BRIEF DESCRIPTION OF THE DRAWINGS

The invention will now be described with reference to the accompanying drawings, in which.

DETAILED DESCRIPTION OF PREFERRED EMBODIMENTS

Figure 1:
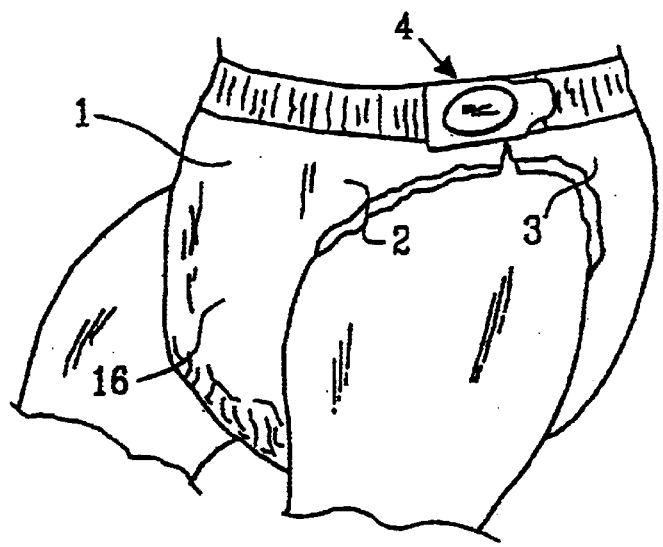
FIG. 1 is a perspective illustration of a donned inventive diaper that includes fastener devices according to a first embodiment of the invention.

FIG. 1 illustrates an inventive diaper 1 donned by the wearer, wherewith the front and rear side-portions 2, 3 have been fastened together by means of fastener devices 4 so as to give the diaper a pants-like configuration. FIG. 1 shows only the left fastener device 4 and the left front and rear side-portions 2, 3 of the diaper. The diaper 1 is of typical construction and includes an inner, liquid-permeable sheet, an outer liquid-impermeable sheet or backing sheet 16, and an absorbent body enclosed between said inner and outer sheets, and includes typically a central part and front and rear side-portions which project out on respective sides of said central part. A more detailed description of the construction of the diaper 1 is unnecessary with respect to obtaining a better understanding of the present invention and will not therefore be given. All of the fastener devices shown in FIGS. 1–5, 9, 10 are fastened to a diaper of similar construction to that described above and corresponding components of the diaper have been identified with the same reference signs in said Figures.

Figure 2:
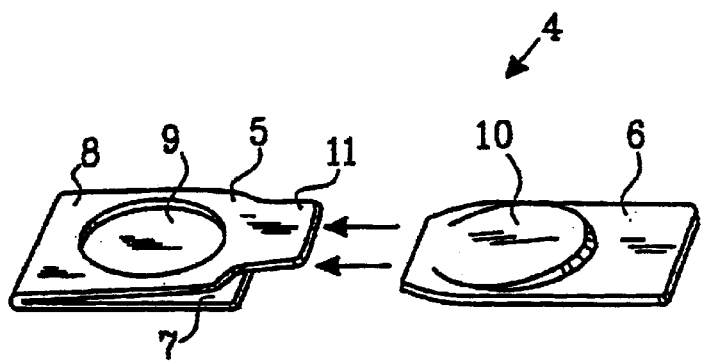
FIG. 2 is a perspective illustration of one of the fastener devices on the diaper shown in FIG. 1, and shows the fastener device in a separated state.

FIG. 2 shows the fastener device 4 on the left in FIG. 1 in larger scale and in a separated state. The device 4 includes a first element 5 which is fastened to the front side-portion 2 of the diaper, and a second element 6 which is fastened to the rear side-portion 3 of the diaper 1. The first element 5 includes an inner wall 7 and an outer wall 8 which diverge relative to one another from one end of the first element, such that the walls will be mutually spaced at the other end of said element. The upper wall 8 includes a through-penetrating aperture 9. The other element 6 is comprised of a generally rectangular plate which includes a raised surface 10 that extends generally from one end, the insertion end, slightly in towards the other end of the plate, the fastening end. The thickness of the raised surface 10 increases towards the fastener end and the thickness of said surface at its highest part is greater than the greatest distance between the walls 7, 8 of the first element 5 within the region of the aperture 9. The shape of the raised surface 10 is complementary to the shape of the aperture 9, at least within the region of the highest edge of said aperture. As the front end of the element 6 (as seen in the Figures) is inserted between the walls of the element 5 in the direction arrowed in FIG. 2, the wall 8 will be flexed outwardly so as to allow passage of the raised surface 10. When the rear edge of the raised surface 10 (as seen in the insertion direction) has passed the rear edge of the aperture 9 (seen in the insertion direction), the wall 8 will spring back to its earlier position by virtue of the elasticity of said wall, wherewith part of the raised surface 10 will project out through the aperture 9 beyond the wall 8 such as to latch the elements 5 and 6 together.

In one variant, the raised surface 10 may include a bead or like premonitory at least around the highest part of its upper edge, so as to eliminate the risk of inadvertently breaking the mechanical connection between the elements 5 and 6. Because the side-portions strive to separate as a result of the spring-back force, the highest part of the edge of said aperture 9 will press against the highest part of the raised surface 10 beneath the bead when the diaper is donned.

The mechanical connection between the elements 5 and 6 can be readily released, simply by lifting the upper wall 8 to an extent such as to release the aperture 9 from its engagement with the raised surface 10. The upper wall 8 is preferably terminated with a gripping tab 11 to this end. When the raised surface 10 has been released from the aperture 9 in the upper wall, the side-portions will separate as a result of said spring-back force and the element 6 will be moved in a direction opposite to the insertion direction relative to the element 5. The diaper is preferably provided with waist elastic in order to obtain the desired spring-back force or re-tensioning force. Naturally, the raised surface 10 can be pressed down towards the lower wall 7 instead of lifting the upper wall 8, in order to move the raised surface out of engagement with the aperture 9. The raised portion 10 is conveniently given a comparatively small wall thickness in order to facilitate this latter release option.

The fastener device provided on the right side of the diaper shown in FIG. 1 is identical to the aforedescribed fastener device 4. It is, of course, possible to fasten the element 6 to the front side-portion of the diaper instead of to its rear side-portion, as shown in the Figure, and to fasten the element 5 to the rear side-portion of the diaper instead of to its front side-portion.

The inventive elements 5, 6 are made of a polymeric material, for instance a material that is comprised of polylactic acid and a plasticizer or softener, such as citric acid ester. The admixture of a plasticizer or softener enhances the suppleness of the material so as to eliminate the risk of a child or other wearer being harmed by the edge of the wall 8. The elements are preferably vacuum formed.

Polymeric material that is based on lactic acid is highly suitable as a material for producing fastener devices for absorbent articles of the aforesaid types. The properties of said material can be readily adapted to the requirements placed on the special fastener devices by adjusting the amount of plasticizer. The material may also be admixed with substances other than a plasticizer in order to obtain a material of desired properties, for instance starch. In one variant, the renewable polymeric material may consist of a copolymer, such as a lactic acid and caprolactone copolymer. The aforesaid polymeric material is also suitable for the manufacture of fastener devices, since it can be readily vacuum formed or moulded.

When ultrasonic welding semicrystalline polymers at material temperatures that exceed the glass transition temperature of the material, the ultrasonic energy applied is absorbed as a result of the visco-elastic energy losses (internal friction) in the material. Visco-elastic energy losses in the material are significant when ultrasonic welding thicker material, such as when welding fastener devices that consist of polyethylene (glass transition temperature about −120° C.) or polypropylene (glass transition temperature about −10° C.), therewith requiring the application of considerable ultrasonic energy in order to obtain a good weld.

In the case of material where ultrasonic welding can be effected at material temperatures below the glass transition temperature of the material, the ultrasonic energy applied is transmitted to the boundary surface and there absorbed so as to melt the material through the medium of external friction. The energy applied is utilised very effectively with such materials, since the energy is absorbed chiefly in the join region. In the case of polylactic acid, which has a glass transition temperature above room temperature (50–60° C.), the ultrasonic energy applied is transmitted chiefly to the boundary surface, or interface, where joining shall take place. Together with the relatively low melting point (140–180° C.), this is highly beneficial from a process aspect, since welding can be effected at very high web speeds. This has significant importance when welding together several sheets of material and when thicker material, such as fastener devices, shall be joined together.

Fastener devices that are based on polylactic acid may also be advantageously used in heat welding processes and have been found to provide strong welds with an energy consumption that is lower than the energy consumed in the case of polypropylene-based material.

The low energy consumption achieved when welding fastener devices based on polylactic acid is, of course, beneficial from an environmental aspect. Because it is difficult generally to weld together materials that have mutually different melting points, the absorbent articles in which the fastener devices are included are also provided with at least one outer sheet which is made of a material that has the same melting point, preferably polylactic acid, wherewith the rear-side layer 16 of the diaper 1 is comprised of a liquid-impervious polylactic acid film and the top-side layer is made of a nonwoven material comprised of polylactic acid fibres. The use of such material also provides a product that can be handled as waste in an environmentally friendly manner.

Figure 3A:
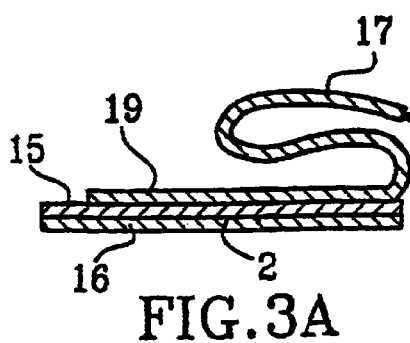
FIGS. 3A–5B are cross-sectional views of other embodiments of inventive fastener devices suitable for use with an inventive diaper.
Figure 3B:
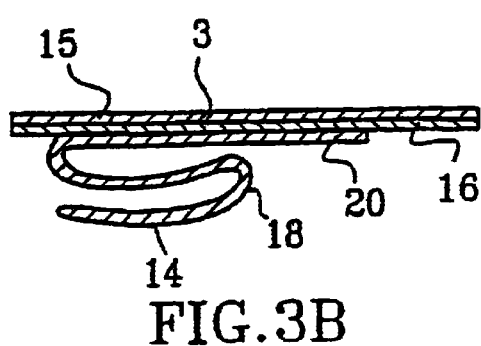
Figure 3C:
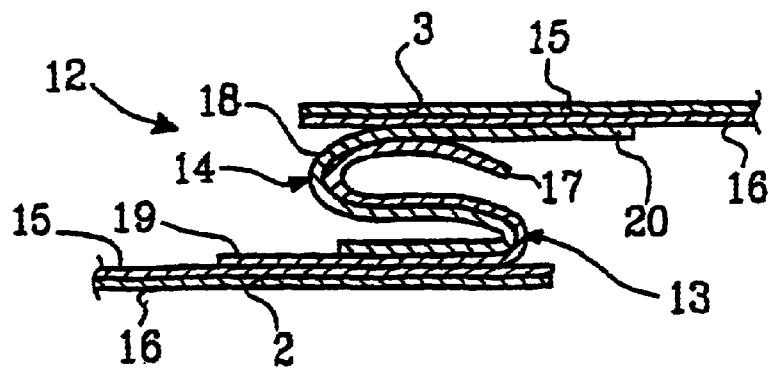

FIGS. 3A–3C are cross-sectional views of a second embodiment of a fastener device 12 that can be used on an inventive diaper 1. Similar to the device 4 of the FIGS. 1 and 2 embodiment, the device 12 includes two band-like fastener elements 13, 14 of which one is fastened to the front side-portion 2 of the diaper (not shown in its entirety) and the other element is fastened to the rear side-portion 3 of the diaper. The fastener elements 13, 14 consist of a fastener part 17, 18 that has an S-shape cross-section, and a rectangular part 19, 20 which forms an extension of one leg of the S-shape part and which is fastened to respective side-portions 2, 3 of the diaper. FIG. 3C shows the fastener elements 13, 14 in an assembled state, i.e. their latching state, with the S-shapes in mutual engagement. As will be apparent from a comparison between FIGS. 3A, 3B and 3C, the S-shapes are slightly straightened out when inserting the parts 17 and 18 into one another. Consequently, in addition to being shape-bound to one another when joined together in their latching positions, the elements 13 and 14 will also be held together by the spring-back force or restoring force generated as the parts 17 and 18 strive to return to their positions shown in FIGS. 3A and 3B. The fastener element 13 is welded to the inner liquid-permeable sheet 15 whereas the fastener element 14 is welded to the outer liquid-impermeable sheet 16 of the diaper.

Figure 4:
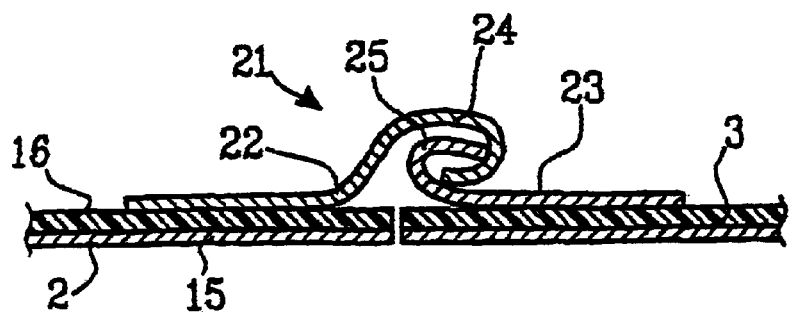

FIG. 4 shows a somewhat simpler variant of a fastener device 21 that can be used with an inventive diaper 1. The fastener device 21 includes fastener elements 22, 23 that have mutually coacting fastener parts 24, 25, said fastener parts having a hook-like cross-sectional shape. In this case, the hooked parts 22, 23 are solely shape-bound to one another. In order to prevent the hooks being moved vertically in relation to one another, one of the band-like fastener elements will preferably be broader than the other element, and the hook-part is sealed at both ends. The ends of one of the band-like elements in FIGS. 3A–3C are also conveniently sealed in the same way. In this embodiment, both of the elements 22, 23 are welded to the outer sheet 16 of the diaper.

Figure 5A:
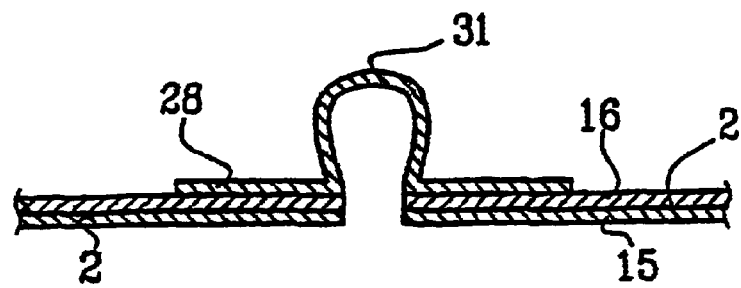
Figure 5B:
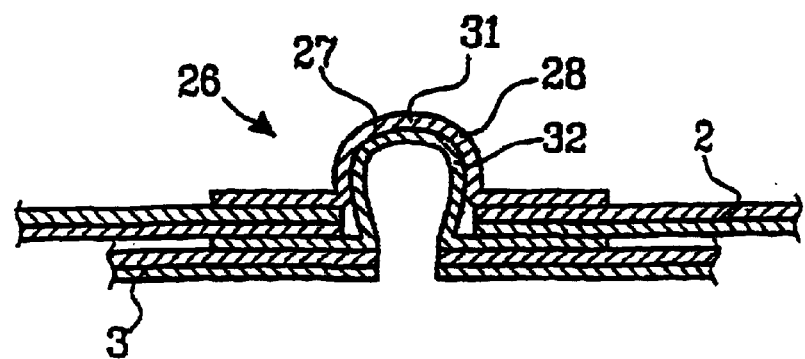

FIG. 5B illustrates a third embodiment of a fastener device 26 that can be used with an inventive diaper 1. The fastener device includes two mutually coacting, band-like fastener elements 8,7 fastened to respective side-portions 2, 3 of the front and rear parts of the diaper. The fastener elements 27, 28 each include a fastener part 31, 32 that extends across the width of said elements and has a keyhole-shaped cross-section, as will best be seen from FIG. 5A, which shows the fastener element 28 in a load free state. The fastener parts are open at their sides that face towards the side-portions 2, 3 of the diaper, so as to form insertion openings, and at least one of the side-portions 2, 3 is slotted in the section beneath the insertion opening. The mutually coacting parts 31, 32 are dimensioned so that they will be held together by means of a snap action, subsequent to the part 31 being pressed onto the part 32. Both of the fastener elements 27, 28 are welded to the outer sheet 16.

Figure 6:
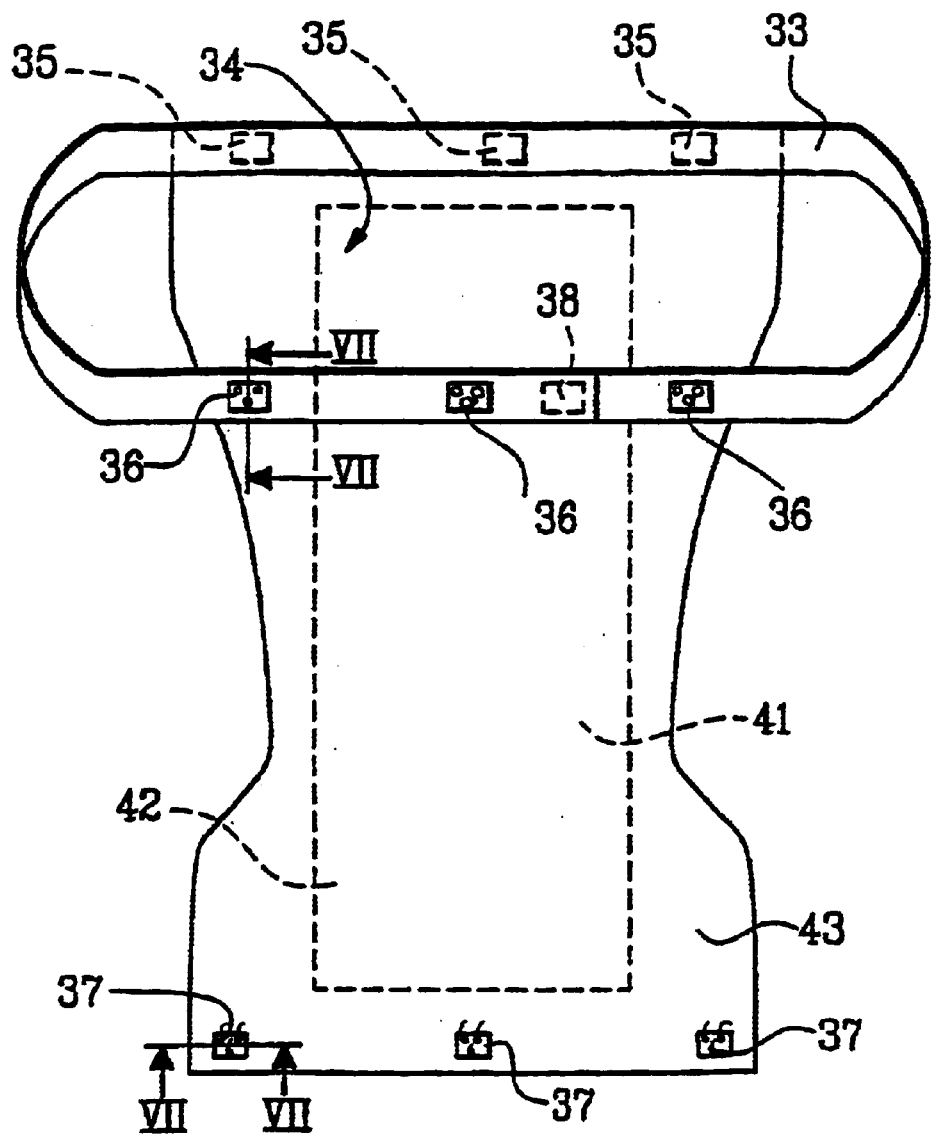
FIG. 6 is a perspective illustration of a waist belt that can be used more than once and shows an absorbent unit which coacts with said belt and which includes inventive fastener devices.

FIG. 6 illustrates a fourth embodiment in which mutually coacting fastener elements have been attached to a waist belt 33 and to an absorption unit 34 respectively. In this case, the fastener devices are of the touch-and-close type 35, i.e. one of the mutually coacting fastener elements 36, 37 includes a multiple of hooked members and the other element includes a multiple of looped members. In the illustrated embodiment, the elements 37 containing hooked members are fastened to the absorption unit, whereas the elements 36 containing the loops are fastened to the waist belt. The waist belt also includes a fastener device 38 for fastening the ends of the belt together, this fastener device 38 being of the touch-and-close type or some other type. The waist belt may be a belt that can be used several times and is made from a soft and skin-friendly material, for instance nonwoven material. The absorption unit 34 is comprised conventionally of an absorbent body 41 enclosed between a liquid-impermeable outer sheet or backing sheet 42 and a liquid-permeable inner sheet or top sheet 43, wherewith at least the inner sheet 43 is made of a renewable material that has a low melting point.

Figure 7:
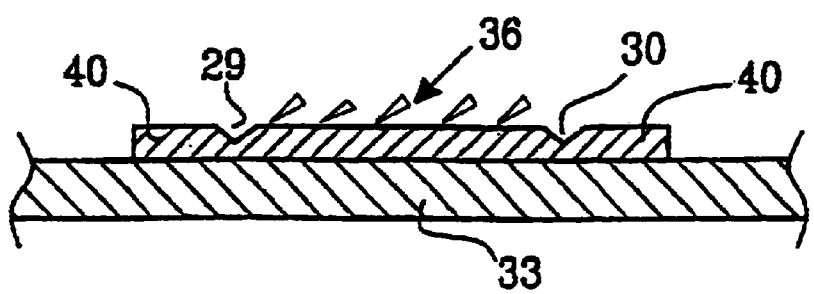
FIG. 7 is a cross-sectional view taken on the line VII—VII in FIG. 6.

When the waist belt is made of a material that will not degrade biologically, it may be suitable to fasten the loop-bearing elements 36 in a manner which enables them to be removed from the belt As will be apparent from FIG. 7, when the waist belt is made of a non-weldable material, the looped fastener elements 36 are fastened to the waist belt 33 solely on its long-edge parts 40, for instance by gluing, and weakening lines 29, 30 are provided between said parts 40 and the central part of the element 36. This enables the elements 36 to be removed from the waist belt prior to it being thrown away.

According to one advantageous variant, the waist belt 33 may be made of a renewable material that will also degrade biologically, so that the entire belt can be treated as waste in an environmentally friendly fashion, in which case the fastener elements 36 will not include weakening lines.

Figure 8:
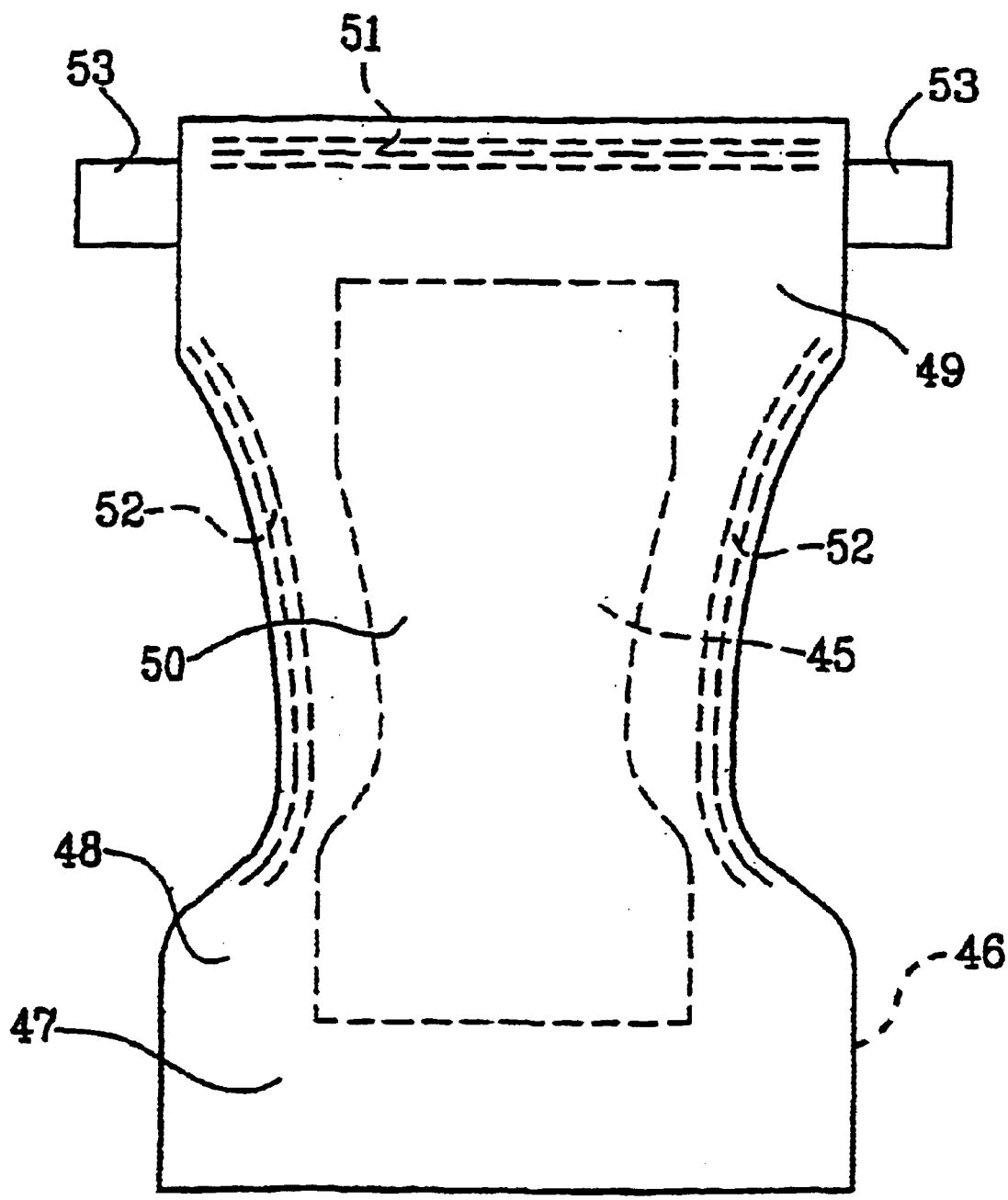
FIG. 8 shows a diaper provided with adhesive tabs in accordance with one embodiment of the invention.

FIG. 8 shows an all-in-one diaper which includes an absorbent body 45 enclosed between a liquid-impervious backing sheet 46 and a liquid-permeable top sheet 47. The diaper also includes a front part 48, a rear part 49 and an intermediate crotch part 50. Elastic threads 51 or ribbons are disposed along the edge of the rear diaper part to form a waist elastic, while elastic threads 52 are disposed along the side-edges of the diaper in the crotch part and in parts of the front and rear parts to form leg elastic. According to the invention, two fastener tabs 53 are provided at the corners of the rear diaper part, said tabs being produced from renewable material of low melting point that lies between 140–180° C., preferably polylactic acid. At least the rear side layer 46 of the diaper is also produced from the renewable material. These tabs are provided with a suitable adhesive so as to enable the side-edges of the diaper in the front and rear parts to be joined together after the diaper has been placed on the user. If the material from which both the inner and outer sheets of the diaper are made is not biologically degradable, the fastener tabs 53 may be releasably attached to the rear-side layer in the same manner as the fastener element 37 of the FIG. 7 embodiment, for instance. This will also apply, of course, to earlier described variants where the fastener elements are welded to one and the same outer sheet.

FIGS. 9a–h show a number of embodiments of individual fastener elements from above, said elements being usable with an inventive diaper 1. Of the illustrated elements, the element 54 of FIG. 9a has an elliptical shape, the element 55 of FIG. 9b an oblong shape, the element 56 of FIG. 9c a square shape, the element 57 of FIG. 9d has a recessed elliptical shape, as will be more apparent from FIG. 10c in which the element 57 is shown in a cross-sectional view from one side. The element 58 of FIG. 9e has the shape of a square combined with segments of a circle, and the element 59 of FIG. 9f has a circular shape. The shape of the element can, of course, be varied infinitely without deviating from the basic concept of enabling two similar elements with a small size difference to be pressed together and therewith achieve a so-called snap-locking effect. In this respect, the slightly smaller so-called male element is pressed into the so-called female element, wherewith at least one of said elements will comprise a material that has a given degree of elasticity.

Figure 9A:
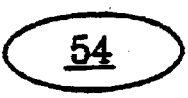
FIGS. 9a–h illustrate from above further embodiments of inventive fastener elements.
Figure 9B:
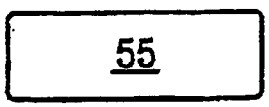
Figure 9C:
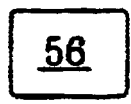
Figure 9D:
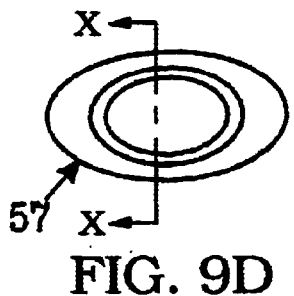
Figure 9E:
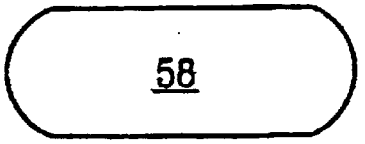
Figure 9F:
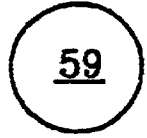
Figures 9G, 9H:
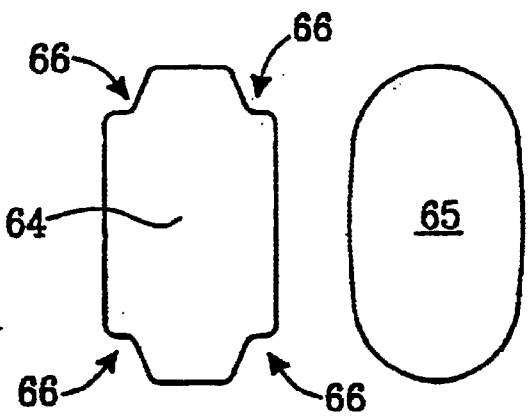
Figure 10A:
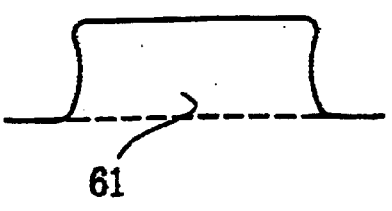
FIGS. 10a–e include schematic cross-sectional views of some other elements including the element in FIG. 9d along line X—X.
Figure 10B:
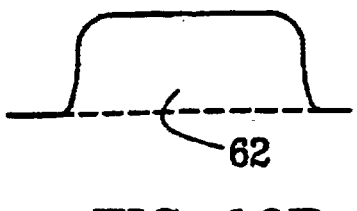
Figure 10C:
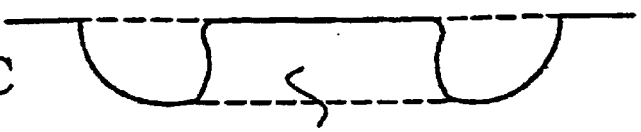
Figure 10D:
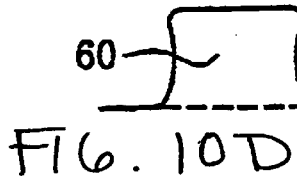
Figure 10E:
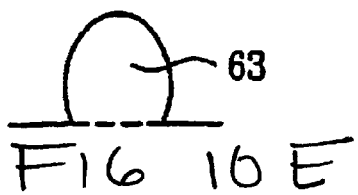

The female and male elements need not have precisely the same shape, but instead may have mutually different shapes. FIG. 9g shows an example of a male element 64 that includes recesses 66 at its respective four corners. This male element 64 is intended to fit into a female element 65 shown adjacent the male element 64 in FIG. 9h. The female element 65 lacks corresponding recesses. Without being limited to any precise theory, it is believed that the walls defining the recesses 66 in the male element 64 can be deformed so as to facilitate insertion of the male element 64 into the female element 65.

FIGS. 10a–e illustrate further examples of fastener elements in cross-section from one side. The fastener elements 57, 60–63 are shown in cross-section to illustrate the form which has a positive effect on the latching facility afforded by the latching elements. In a preferred embodiment, the fastener elements are produced by drawing parts of discrete pieces of material into air-permeable moulds by suction and therewith form cavities, so-called vacuum forming, wherewith the material can also be heated to improve its shapability if necessary. The fastener elements shown in FIGS. 9a–h and 10a–e can either be welded to one and the same outer sheet analogously with the fastener elements 27, 28 shown in FIGS. 5A, 5B, or welded to different outer sheets.

It will be understood that the invention is not restricted to the described and illustrated embodiments and that these embodiments can be modified within the scope of the invention, particularly with respect to the design of the fastener elements of the fastener devices and also with respect to the material from which these devices and the outer sheets are made. The invention is therefore only restricted by the contents of the accompanying Claims.

What is claimed:

1. An absorbent article having a front part, a rear part and an intermediate central part, said article including an absorbent body enclosed between an inner, liquid-permeable sheet and a liquid-impermeable outer sheet, and fastener devices for releasably connecting side-portions of the front and rear parts located on a same side of a longitudinal symmetry line of said article either directly or indirectly, said fastener devices being made of a renewable material, wherein the fastener devices are fastened by welding to at least one of the sheets of said article; and wherein the fastener devices and said at least one of the or sheets to which the fastener devices are fastened are made of a material having a glass transition temperature which lies between 50–60° C. and a melting point which lies between 140–180° C.

2. The article according to claim 1, wherein the fastener devices and the sheet or sheets to which the fastener devices are fastened are at least made mainly of polylactic acid.

3. The article according to claim 1, wherein each of the fastener devices include two mutually coacting elements of which one element is fastened to the front part side-portion of the article and the other is fastened to the rear part side-portion of said article; and wherein the mutually coacting elements are fastened to the same sheet of said article.

4. The article according to claim 1, wherein the fastener devices each include two mutually coacting elements of which one element is fastened to the front side-portion of the article and the other is fastened to the rear side-portion of said article;

wherein the mutually coacting elements are fastened to different sheets; and wherein both sheets are made of a material that has a glass transition temperature which lies between 50–60° C. and a melting point which lies between 140–180° C.

5. The article according to claim 4, wherein the melting point is between 150–175° C.

6. The article according to claim 1, wherein the fastener devices are made from one of the materials polylactic acid, a copolymer of lactic acid, plasticized or softened polylactic acid or a laminate consisting of a combination of the aforesaid materials.

7. The article according to claim 1, wherein the fastener devices include two mechanically coacting fastener elements;

wherein one of said fastener elements includes a part which projects out from a longitudinal plane of said element and which can be inserted into an aperture or recess of corresponding shape in said second element, wherein the insertion direction is parallel with said longitudinal plane of said element; and wherein the fastener elements are fastened to the liquid-impermeable outer sheet.

8. The article according to claim 1, wherein each of the fastener devices includes two mechanically coacting fastener elements;

wherein the fastener elements include hooked parts of mutually complementary shape; and wherein the fastener elements are fastened to different sheets.

9. The article according to claim 1, wherein each of the fastener devices includes two mechanically coacting fastener elements; and wherein the fastener elements include parts that can be snapped into one another.

10. The article according to claim 1, wherein each of the fastener devices includes two mechanically coacting fastener elements; and wherein the fastener elements include hook and loop members.

11. The article according to claim 1, wherein each of the fastener devices is comprised of an adhesive fastener tab.

12. The article according to claim 1, wherein the melting point is between 150–175° C.

* * * * *